(12) United States Patent
Mazurek et al.

(10) Patent No.: US 6,387,952 B1
(45) Date of Patent: May 14, 2002

(54) METHOD OF TREATING GASTROINTESTINAL DISORDERS, PARTICULARLY COLITIS

(75) Inventors: Harry Mazurek, Bala Cynwyd, PA (US); Robert W. Harkins, North Brunswick, NJ (US)

(73) Assignee: ARCO Chemical Technology L.P., Greenville, DE (US)

( * ) Notice: Subject to any disclaimer, the term of this patent is extended or adjusted under 35 U.S.C. 154(b) by 0 days.

(21) Appl. No.: 09/664,172

(22) Filed: Sep. 19, 2000

(51) Int. Cl.$^7$ ................................................ A01N 37/02
(52) U.S. Cl. ....................................... 514/552; 554/227
(58) Field of Search ........................... 514/552; 554/227

(56) References Cited

U.S. PATENT DOCUMENTS

| | | | |
|---|---|---|---|
| 4,861,613 A | * | 8/1989 | White et al. ................. 426/611 |
| 4,983,329 A | | 1/1991 | Cooper |
| 5,175,323 A | | 12/1992 | Cooper |
| 5,569,680 A | | 10/1996 | Wu |
| 5,986,117 A | | 11/1999 | Cooper |

OTHER PUBLICATIONS

W. Scheppach, H.P. Bartram and F. Richter, "Role of Short–chain Fatty Acids in the Prevention of Colorectal Cancer", Eur J. Cancer, vol. 31A, No. 7/8, pp. 1077–1080, 1995.

W. Scheppach, S.U. Christl, H.–P. Bartram, F. Richter & H. Kasper, "Effects of Short–Chain Fatty Acids on the Inflamed Colonic Mucosa", Scand. J. Gastroenterol, Suppl. 222, pp. 53–57 (1997).

J.R. Jorgensen and P.B. Mortensen, "Influence of Feces from Patients with Ulcerative Colitis on Butyrate Oxidation in Rat Colonocytes", Digestive Diseases and Sciences, vol. 44, 10 pp. 2099–2109 (1999).

Richard V. Perez et al., "Selective Targeting of Kupffer Cells With Liposomal Butyrate Augments Portal Venous Transfusino–Induced Immunosuppression[1,2], Transplantation", vol.. 65, 10, p. 1294–1298, 1998.

Richard Perez et al., "Sodium Butyrate Upregulates Kupffer Cell $PGE_2$ Production and Modulates Immune Function[1]", J. Surgical Res., 78 pp. 1–6 (1998).

Steven M. Watkins et al., "Butyric acid and tributyrin induce apoptosis in human hepatic tumour cells", J. Dairy Res., 66 pp. 559–567 (1999).

G.H. Rabbani et al., "Short–Chain Fatty Acids Inhibit Fluid and Electrolyte Loss Induced by Cholera Toxin in Proximal Colon of Rabbit In Vivo", Digestive Diseases and Sci., vol. 44, 8, pp. 1547–1553 (1999).

Janet G. Smith et al., "Butyric Acid from the Diet: Actions at the Level of Gene Expression", Crit. Rev. in Food Sci., vol. 38, 4, pp. 259–297 (1998).

Young–In Kim, "Short–Chain Fatty Acids In Ulcerative Colitis", Nutrition Reviews, vol. 56, 1, pp. 17–24,1998.

K.H. Soergel, "Colonic fermentation: metabolic and clinical implications", CLN Investig 72, 742–48 (1994).

W. Scheppach, "Effects of short chain fatty acids on gut morphology and function", GUT 1994, Supplement 1, pp. 35–38.

* cited by examiner

*Primary Examiner*—Deborah D. Carr
(74) *Attorney, Agent, or Firm*—Brooks & Kushman P.C.

(57) ABSTRACT

Administration of alkoxylated acyl glycerine (AAG) containing lower carboxylic acid acyl moieties to mammalian subjects results in increase of lower carboxylate concentration, particularly in the colon, and may be used to treat such disorders as simple colitis, ulcerative colitis, divertive colitis, colorectal cancer, and other diseases of the gastrointestinal tract where lower carboxylates are implicated. The AAG encourage patient compliance due to substantially no odor, even when butyric acid acyl groups are employed.

20 Claims, No Drawings

METHOD OF TREATING GASTROINTESTINAL DISORDERS, PARTICULARLY COLITIS

TECHNICAL FIELD

The present invention is directed to treating gastrointestinal disorders, including inflammatory bowel disease, particularly colitis, and to methods of increasing the short chain fatty acid content of the colon.

BACKGROUND ART

It is now well recognized that short chain fatty acids (SCFA), particularly those having from 1 to 4 carbon atoms are implicated in the treatment of numerous diseases and/or conditions of the gastrointestinal tract, particularly the colon. It is universally accepted that SCFA are a major energy source for the colon and other related tissues.

SCFA are liberated on the bodies of mammals predominately through the anaerobic fermentation of undigested carbohydrates in the colon. Of the SCFA, acetic acid, propionic acid, and butyric acid account for 90–95% of SCFA in the colon. Kim, Young-In, "Short-Chain Fatty Acids in Ulcerative Colitis", NUTRITION REVIEWS, Vol. 56, 1, pp. 17–24. The ratio of acetic ("acetate") to propionic ("propionate") to butyric ("butyrate") acids is about 1:0.31:0.15, and the proportions vary with the substrate (largely roughage), composition of anaerobic flora, and pH. However, the fermentation products are remarkably similar in the human colon, the large cecum of herbivores, and bovine rumen. Soergel, K. H., "Colonic Fermentation: Metabolic and Clinical Implications", CLIN INVESTIG 72, 742–48 (1994). Deficiencies in SCFA have been associated with inflamed colonic mucosa, Sheppach, W., et al., "Effects of Short-Chain Fatty Acids on the Inflamed Colonic Mucosa", SCAND. J. GASTROENTEROL, Suppl. 222, pp. 53–57 (1997) and ulcerative colitis, W. Sheppach, "Short-Chain Fatty Acids Improve Epithelia in Ulcerative Colitis? Speculation or Mechanism", Falk Symp. (1994), 73 (Short Chain Fatty Acids), pp. 206–213; diversion colitis, Soergel, op. cit.; and other disorders.

Studies have shown that increasing SCFA levels brings about therapeutically significant improvements in areas such as prevention of Colorectal Cancer, W. Sheppach, et al. "Role of Short-Chain Fatty Acids in the Prevention of Colorectal Cancer", EUR J. CANCER, Vol. 31A, No. 7/8, pp. 1077–80, 1995; treatment of colitis, W. Sheppach, "Effects of Short Chain Fatty Acids on Gut Morphology and Function", GUT 1994, Supplement 1, pp. 35–38; ulcerative colitis, Jorgersen, J. R., et al., "Influence of Feces from Patients with Ulcerative Colitis on Butyrate Oxidation in Rat Colonocytes", DIGESTIVE DISEASES AND SCIENCES, Vol. 44, 10 pp. 2099–2109 (1999), Kim, op. cit., Sheppach, Falk Symp. (1994), 73 (Short Chain Fatty Acids), op. cit. (pp. 206–213); and diversion colitis Soergel, op. cit. In addition, SCFA's are implicated in immune system response, Perez, R., et al. "Selective Targeting of Kupffer Cells with Liposomal Butyrate Augments Portal Venous Transfusion-Induced Immunosuppression", TRANSPLANTATION, Vol. 65, 10, p. 1294–98, 1998; Perez, R., et al. "Sodium Butyrate Upregulates Kupffer Cell $PGE_2$ Production and Modulates Immune Function", J. SURGICAL RES., 78 pp. 1–6 (1998); apoptosis in hepatic tumors, Watkins, S. M., et al.; "Butyric Acid and Tributyrin Induce Apoptosis in Human Hepatic Tumor Cells", J. Dairy Res., 66, pp. 559–67 (1999); and in inhibiting fluid loss in chloera-infected mammals, Rabboni, G. H., et al., "Short-Chain Fatty Acids Inhibit Fluid and Electrolyte Loss Inducted by Cholera Toxin in Proximal Colon of Rabbit In Vitro", DIGESTIVE DISEASES AND SCI., Vol. 44, 8, pp. 1547–53 (1999).

In most studies reported above, SCFA were administered in the form of their soluble salts, i.e., alkali metal acetates, propionates, and butyrates. The "ate" salt suffix has been used rather uniformly in the medical literature to refer to both the salt and free acid forms of the SCFA, unless indicated to the contrary.

Administration of SCFA, notably butyrate, both in oral form and as an enema or suppository, has been found to affect a variety of disorders, as indicated above. However, butyric acid and its salts are notoriously odorous, so much so that patients often discontinue treatment because of the foul odors involved. In U.S. Pat. No. 5,569,680, administration of glycerine tris(butyrate ester), known as tributyrin, is said to improve patient compliance through use of a less odiferous substance. However, tributyrin is still somewhat odiferous, perhaps due to incomplete esterification, or due to partial hydrolysis liberating butyric acid. Thus, the administrative problems of butyrate, while ameliorated by tributyrin, are not completely solved by its use. Moreover, as indicated by Smith, J. G., et al. "Butyric Acid from the Diet: Actions at the Level of Gene Expression", CRIT. REV. IN FOOD SCI., Vol. 38, 4, pp. 259–97 (1998), the effects of butyrate derivatives such as arginine butyrate, butyramide, monobutyrin, and tributyrin are not the same, and thus additional butyrate-releasing compounds are desired.

DISCLOSURE OF INVENTION

The present invention pertains to a method of increasing the short chain fatty acid (SCFA) content of the gastrointestinal tract, in particular the colon. The present invention also pertains to a method for treating various gastrointestinal disorders by supplying a substantially odor-free compound which can be absorbed and/or metabolized in situ in the gastrointestinal tract to liberate SCFA, and to compounds suitable for use therein.

BEST MODE FOR CARRYING OUT THE INVENTION

The compounds of the subject invention which are useful in treating gastrointestinal disorders are alkoxylated acyl glycercol (AAG) which correspond to the formula

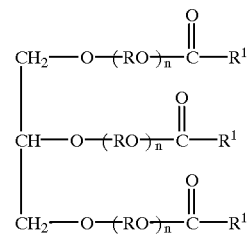

where each n individually is an integer from 0 to 5, preferably from 1 to 3, and most preferably from 1 to 2, R is

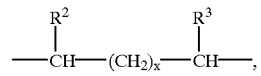

wherein x is 0 to 2, preferably 0, wherein $R^2$ and $R^3$ individually are H or $C_{1-4}$ lower alkyl, preferably H, —$CH_3$ or —$CH_2CH_3$, and most preferably hydrogen and —$CH_3$; and wherein $R^1$ is H or $C_{1-6}$ lower alkyl, preferably $C_{1-4}$ lower alkyl, more preferably $C_{2-4}$ lower alkyl, and most preferably —$CH_2CH_2CH_3$. One or two of $R^1$ may be a $C_{7-23}$ alkyl or alkenyl group; however, at least one $R^1$ is $C_{1-6}$ lower alkyl. Preferably at least two $R^1$ on average are $C_{1-6}$ lower alkyl, and most preferably all three $R^1$ are n-$C_3$ lower alkyl. The use of an enantiomerically pure alkylene oxide starting material in the synthesis will result in an enantiomerically enriched alkoxylated acyl glycerol. The compounds of the subject invention are absorbable and/or digestible in the gastrointestinal tract, particularly in the colon, to liberate free carboxylic acid of the formula

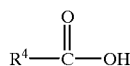

or a salt or derivative thereof, where $R^4$ is $C_{1-6}$ lower alkyl, more preferably $C_{1-4}$ lower alkyl, most preferably n-$C_3$.

The compounds of the subject invention are thus lower carboxylic acid esters of polyoxyalkylated glycerine, wherein the polyoxyalkylene groups are derived from ethylene oxide, propylene oxide, 1,2- and 2,3-butylene oxide, tetrahydrofuran and the like, with preference being given to those derived from propylene oxide or mixtures of propylene oxide and ethylene oxide. It is imperative that the subject compounds liberate free lower carboxylic acid, its carboxylate anion, or salt thereof upon "digestion" or "hydrolysis" in the gastrointestinal tract, or be absorbed within the gastrointestinal tract and metabolized in colonic tissue or in other organs. The compounds of the subject invention may first be metabolized to intermediates which are further metabolized to SCFA. The suitability of such compounds for use in the subject invention may be assessed by analytical techniques as discussed herein, and by other conventional techniques. The molecular weight of the products are preferably below 600–900 Daltons (Da), preferably below 450 Da.

Preferred AAG are propoxylated acyl glycerols, "PAG":

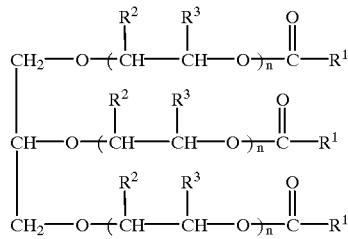

where $R^2$ and $R^3$ individually are H or $CH_3$, and at least one of $R^2$ and $R^3$ is $CH_3$. PAG are prepared by oxypropylating glycerine followed by acylation.

The compounds of the subject invention may be prepared by the same techniques as disclosed in U.S. Pat. Nos. 4,983,329; 5,175,323; and 5,986,117, all incorporated herein by reference, except that the higher alkyl carboxylic acids in those syntheses are replaced by lower carboxylic acids, and the degree of oxyalkylation is reduced so as to provide a digestible rather than an indigestible product. Surprisingly, the subject compounds substantially survive digestion in the small intestine, and thus their full complement of SCFA becomes available to the colon and associated organs.

Digestability and absorbability may be assessed by numerous tests. Two useful tests are digestability measured in vitro by pancreatic lipase enzyme, and fecal matter tests.

Since lower alkyl carboxylic acids are rapidly metabolized, the amounts present in expelled feces will ordinarily be lower than that present in the upper and mid colon and other portions of the gastrointestinal tract. The amount of free carboxylic acid may also be monitored by feeding appropriately radio-tagged AAG and measuring the relative amounts of radio-tagged excretion products. Many other techniques will be immediately apparent to those skilled in the art of monitoring digestive processes and drug uptake and retention.

Digestability by Pancreatic Lipase

Following the procedure of U.S. Pat. No. 4,983,329, a number of potential PAG products are prepared in which n is varied in the range of from 1–8 by control of the amount of propylene oxide (PO) in the reaction. 100 mg of the PAG is added to 10 ml of buffer containing 1 mM naCl, 1 mM $CaCl_2$, 3 mM deoxycholate, 2 mM tris, and 10 g/l of gum arabic. The mixture is vigorously shaken in a capped test-tube, and the emulsion transferred to a pH stat reaction vessel. The pH is titrated to 8.0 using a Tadiometer pH stat (comprising a TTA80 titration assembly, a TTT80 titrator, and ABU80 autoburette and a pHM82 pH meter). Porcine pancreatic lipase (0.1 ml, equivalent to 1000 units of enzyme, at pH 8.0) is added, the pH rapidly re-equilibrated to 8.0, and then the reaction is followed over a 20 minute period by autotitration with 50 mM aqueous NaOH. The initial, linear rate is reported as micro moles of NaOH per hour required to keep the pH constant by neutralizing the free fatty acids released by the action of pancreatic lipase.

Based on the data collected, when n=3, the lipase hydrolysis rate is about 10%, and at n=4 it is about 5%. These values of n are the sum of all n in the molecule. Thus, digestible PAG containing only oxypropylene residues as oxyalkylene moieties is limited to those having not more than about 5 oxypropylene groups.

The corresponding acetate adducts of ($R^1$=$CH_3$ of several PAG (n-1,2.2, and 5) were assayed by Gas Liquid Chromatography (packed column) to show the distribution of polypropylene oxide units in each. The results are presented below.

TABLE 1

| Average Total n (moles PO) | Free Glycerine | Oxypropylene Units Per Glycerine | | | | | | | |
|---|---|---|---|---|---|---|---|---|---|
| | | 1:1 | 1:2 | 1:3 | 1:4 | 1:5 | 1:6 | 1:7 | 1:8 |
| 1 | 31.1 | 46.2 | 19.9 | 2.7 | | | | | |
| 2.2 | 2.1 | 22.7 | 40.5 | 28.0 | 5.9 | 0.7 | | | |
| 5 | N.D. | N.D. | 1.4 | 16.1 | 34.5 | 28.5 | 13.6 | 5.1 | 0.8 |

In the Table above, the components represent 90% of the mass trace integral. The area % is not corrected to give mass or mole % (FID response factors unknown). The data shows that oxyalkylation always produces a range of products having a statistical distribution of oxyalkylene moieties per mole of glycerine starter. Free glycerine and higher oxyalkylated molecules can be removed by suitable purification techniques if desired. "N.D." means "not detected". By the term "on average" with respect to n, the degree of oxyalkylation, or for PAG, the degree of oxypropylation, is meant the average value of n over the entire population, as determined by GPC.

Digestability by Fecal Analysis

Sprague-Dawley weanling rats (male) are fed a laboratory chow diet containing 2.5% by weight of the test compounds, for example an n=2.2 composition or an n=5 composition, each containing 18% of heptadecanoic acid as a marker, the balance of the fatty acid (acyl) moiety in the test compound being butyric acid. Total dietary lipid is kept at 10% (by weight) with 2.75% added corn oil, the laboratory chow already containing 4.5% lipid. Also, a known non-digestible marker compound, 1,2-didodecyl-3-hexadecyl glycerol, is added to the diets at 0.25% (by weight) level.

Feces are collected and analyzed for lipid content, using a GLC method based on heptadecanoic acid and 1,2-didodecyl-3-hexadecyl-glycerol markers.

The amount of AAG administered to a mammal in need thereof will depend on several factors, all of which can be routinely assessed. For example, the digestibility of the AAG products is inversely proportional to the number of oxyalkylene groups in the molecule, with AAG containing 6 or more oxyalkylene groups substantially undigestible. Thus, AAG with from 2 to 4 oxyalkylene groups are generally optimal, although those with two oxyalkylene groups on average will show a considerably greater rate of hydrolysis or digestion to free fatty acid than those with 4 oxyalkylene groups.

The amount of AAG administered will also depend on the severity of the symptoms. Those with only minor symptoms will likely benefit from lower amounts of AAG, while those with more severe symptoms will generally require larger amounts. The nature and distribution of the acyl groups will also affect dosage, as will the body weight of the mammal, preferably human, receiving the AAG. The amounts will likewise depend upon the type of symptoms treated, i.e., colitis (inflamed colon), ulcerative colitis, colon cancer, divertive colitis, Crohn's Disease, etc., and the mode of administration, i.e., oral, enema, suppository, etc. For example, in enema treatments, the concentration of butyrate may be from 20 mM to 160 mM, with preferable concentration in the range of 60 mM to 100 mM. For a propoxylated butyric acid glycerol triester which is 33% metabolized, the concentration of the PAG in mM should be substantially the same as the desired butyrate concentration. For similar PAG which is 100% metabolized, the PAG concentration will be one third that of the desired butyrate concentration.

In general, oral administration of AAG will range from 0.01 to 5 g/Kg of body weight, more preferably from 0.02 to 2.5 g/Kg body weight. However, amounts outside these ranges may also be useful. For administration as a suppository, amounts of from 0.05 to 0.2 g/Kg body weight is preferred. For human subjects, the entire, normal size suppository may be made of AAG, or a portion may contain other pharmaceutically acceptable ingredients.

The AAG may be administered alone or in conjunction with other medication. For example, 5-aminosalicylic acid and corticosteroids may be useful. Hangauer, S. G., "Inflammatory Bowel Disease", N. ENGL. J. MED., 334 pp. 8414–848 (1996; Gionchehi, P. et al., "Medical Treatment of Ulcerative Colitis", Curr. Opin. Gastroenterol, 12, pp. 352–255 (1996).

Administration of AAG will increase the availability of acylate, preferably butyrate, to the gastrointestinal tract. Treatment of disease or disease symptoms may be monitored appropriately. Because of the decreased rapidity of hydrolysis due to the presence of oxyalkylene groups between the glycerol and butyrate moieties, the AAG have essentially no odor, even upon storage, and thus patient compliance is expected to be high.

The AAG may be administered alone or in combination with other pharmaceutically acceptable ingredients. Unlike butyrate itself, and tributyrin, the subject invention AAG may be incorporated into numerous food products which form a portion of the ordinary diet, for example margarine, baked goods, fried foods, confections, etc. Thus, administration may be substantially "transparent" to the patient.

AAG may be administered alone, or in combination with other pharmaceutically acceptable ingredients, to those not yet exhibiting gastrointestinal disorders, as means of prophylactically administering SCFA's, particularly butyrate, to the gastrointestinal tract.

By the term "associated organ" is meant an organ which derives lower carboxylate from the colon, for example by absorbtion into or diffusion through the colon. By "lower carboxylate" is meant a $C_{1-7}$ carboxylic acid or salt or natural derivative thereof.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An alkoxylated acyl glycerol (AAG) useful for administration to mammalian subjects having a need for increased gastrointestinal lower carboxylate, comprising a compound of the formula

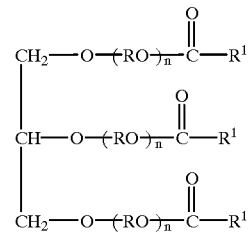

wherein each n individually is an integer from 1 to 5, R is

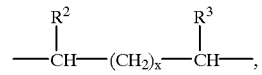

wherein x is an integer from 0 to 2, wherein $R^2$ and $R^3$ individually are H or $C_{1-4}$ lower alkyl, wherein $R^1$ is H or $C_{2-6}$ lower alkyl; one or two of $R^1$ may be a $C_{7-24}$ alkyl or alkenyl group; with the proviso that at least one $R^1$ is $C_{2-6}$ lower alkyl, the compounds are absorbable and/or digestible in the gastrointestinal tract or associated organs to liberate free carboxylic acid of the formula

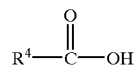

where $R^4$ is $C_{2-6}$ lower alkyl.

2. The AAG of claim 1, wherein one of $R^2$ and $R^3$ is —$CH_3$ and the other of $R^2$ and $R^3$ is H.

3. The AAG of claim 1 wherein on average the total of all n is from 2 to 5.

4. The AAG of claim 1, wherein not more than 1.5 groups (RO) on average contain R other than 2-methylethylene or 1-methylethylene.

5. The AAG of claim 1, wherein at least 2 of $R^1$ on average are n-$C_3$ alkyl groups.

6. The AAG of claim 1, wherein from 0.5 o 1.5 of $R^1$ on average are $C_{11-23}$ alkyl groups or $C_{11-23}$ alkenyl groups.

7. The AAG of claim 1, wherein all —(RO)— are derived from propylene oxide, the sum of all n ranges from 1.5 to 4, and $R^1$ is n-$C_3$ alkyl.

8. A process for increasing the lower carboxylate content of the gastrointestinal tract of a mammal, comprising administering a lower carboxylate-increasing amount of an alkoxylated acyl glycerol (AAG) comprising:

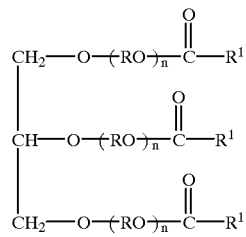

wherein each n individually is an integer from 1 to 5, R is

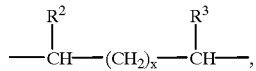

wherein x is an integer from 0 to 2, wherein $R^1$ and $R^3$ individually are H or $C_{1-4}$ lower alkyl, wherein $R^1$ is H or $C_{1-6}$ lower alkyl; one or two of $R^1$ may be a $C_{7-24}$ alkyl or alkenyl group; with the proviso that at least one $R^1$ is $C_{1-4}$ lower alkyl, the compounds are absorbable and/or digestible in the gastrointestinal tract or associated organs to liberate free carboxylic acid of the formula

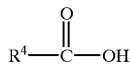

where $R^4$ is $C_{1-6}$ lower alkyl.

9. A process for increasing the lower carboxylate content of the gastrointestinal tract of a mammal, comprising administering a lower carboxylate-increasing amount of the AAG of claim 8 wherein one of $R^2$ and $R^3$ is —$CH_3$ and the other of $R^2$ and $R^3$ is H.

10. A process for increasing the lower carboxylate content of the gastrointestinal tract of a mammal, comprising administering a lower carboxylate-increasing amount of the AAG of claim 8 wherein at least two of $R^1$ on average are n-$C_3$ alkyl groups.

11. A process for increasing the lower carboxylate content of the gastrointestinal tract of a mammal, comprising administering a lower carboxylate-increasing amount of the AAG of claim 8 wherein all —(RO)— are derived from propylene oxide, the sum of all n on average ranges from 1.5 to 4, and $R^1$ is n-$C_3$ alkyl.

12. The process of claim 8 wherein the lower carboxylate content in the colon is increased.

13. A method of ameliorating a medical disorder caused by low lower carboxylate availability in the gastrointestinal tract or associated organs or treatable by raising concentration of lower carboxylate in the lower gastrointestinal tract or associated organs, said method comprising administration to a patient exhibiting symptoms of said medical disorder a lower carboxylate increasing amount of an alkoxylated acyl glycerol AAG having the formula:

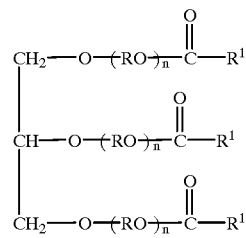

wherein each n individually is an integer from 1 to 5, R is

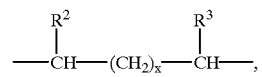

wherein x is an integer from 0 to 2, wherein $R^2$ and $R^3$ individually are H or $C_{1-4}$ lower alkyl, wherein $R^1$ is H or $C_{1-6}$ lower alkyl; one or two of $R^1$ may be a $C_{7-24}$ alkyl or alkenyl group; with the proviso that at least one $R^1$ is $C_{1-6}$ lower alkyl, the compounds are absorbable and/or digestible in the gastrointestinal tract or associated organs to liberate free carboxylic acid of the formula

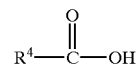

where $R^4$ is $C_{1-6}$ lower alkyl.

14. A method of ameliorating a medical disorder caused by low lower carboxylate availability in the gastrointestinal tract or associated organs or treatable by raising concentration of lower carboxylate in the lower gastrointestinal tract or associated organs, said method comprising administration to a patient exhibiting symptoms of said medical disorder a lower carboxylate increasing amount of the AAG of claim 13, wherein one of $R^2$ and $R^3$ is H and the other of $R^2$ and $R^3$ is $CH_3$.

15. A method of ameliorating a medical disorder caused by low lower carboxylate availability in the gastrointestinal tract or associated organs or treatable by raising concentration of lower carboxylate in the lower gastrointestinal tract or associated organs, said method comprising administration to a patient exhibiting symptoms of said medical disorder a lower carboxylate increasing amount of the AAG of claim 13, wherein at least two of $R^1$ on average are n-$C_3$ alkyl groups.

16. A method of ameliorating a medical disorder caused by low lower carboxylate availability in the gastrointestinal tract or associated organs or treatable by raising concentration of lower carboxylate in the lower gastrointestinal tract or associated organs, said method comprising administration to a patient exhibiting symptoms of said medical disorder a lower carboxylate increasing amount of the PAG of claim 13, wherein all —(RO)— are derived from propylene oxide, the sum of all n on average ranges from 1.5 to 4, and $R^1$ is n-$C_3$ alkyl.

17. The method of claim 13, wherein 5-aminosalicylic acid and/or one or more corticosteroids are administered concurrently.

18. A method of prophylactsis of the gastrointestinal tract of a mammal against gastrointestinal disorders, comprising administering to said mammal a prophylactic amount of an alkoxylated acyl glycerol (AAG) having the formula:

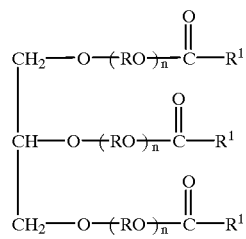

wherein each n individually is an integer from 1 to 5, R is

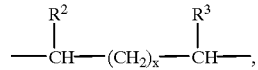

wherein x is an integer from 0 to 2, wherein $R^2$ and $R^3$ individually are H or $C_{1-4}$ lower alkyl, wherein $R^1$ is H or $C_{1-6}$ lower alkyl; one or two of $R^1$ may be a $C_{7-24}$ alkyl or alkenyl group; with the proviso that at least one $R^1$ is $C_{1-6}$ lower alkyl, the compounds are absorbable and/or digestible in the gastrointestinal tract or associated organs to liberate free carboxylic acid of the formula

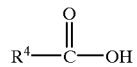

where $R^4$ is $C_{1-6}$ lower alkyl.

19. The method of claim 18 wherein all —(RO)— are derived from propylene oxide.

20. The method of claim 18 wherein at least two of $R^1$ are n-$C_3$.

* * * * *

UNITED STATES PATENT AND TRADEMARK OFFICE
CERTIFICATE OF CORRECTION

PATENT NO. : 6,387,952 B1  
DATED : May 14, 2002  
INVENTOR(S) : Harry Mazurek et al.

It is certified that error appears in the above-identified patent and that said Letters Patent is hereby corrected as shown below:

<u>Column 7,</u>  
Line 1, "0.5 o 1.5 of $R^1$" should read -- 0.5 to 1.5 of $R^1$ --; and  
Line 29, "wherein $R^1$ and $R^3$" should read -- wherein $R^2$ and $R^3$ --.

Signed and Sealed this

First Day of October, 2002

Attest:

Attesting Officer

JAMES E. ROGAN  
*Director of the United States Patent and Trademark Office*